United States Patent [19]

Turk et al.

[11] B  3,996,262

[45] Dec. 7, 1976

[54] METHOD OF PROMOTING THE REACTION OF UNSATURATED NITRILES WITH OLEFINS TO PRODUCE UNSATURATED NITRILES OF INCREASED CARBON NUMBER

[75] Inventors: Stanley D. Turk; Charles A. Drake, both of Bartlesville, Okla.

[73] Assignee: Phillips Petroleum Company, Bartlesville, Okla.

[22] Filed: Apr. 1, 1974

[21] Appl. No.: 456,900

[44] Published under the second Trial Voluntary Protest Program on February 3, 1976 as document No. B 456,900.

Related U.S. Application Data

[63] Continuation-in-part of Ser. No. 210,228, Dec. 20, 1971, abandoned.

[52] U.S. Cl. .............................. 260/465.9; 260/464; 260/465 K
[51] Int. Cl.$^2$ ....................................... C07C 120/00
[58] Field of Search ................ 260/465.8 D, 465.4, 260/464, 465 D, 465.9, 465 K, 465.8

[56]  References Cited

UNITED STATES PATENTS

| | | | |
|---|---|---|---|
| 2,641,607 | 6/1953 | Albisetti, Jr. et al. | 260/465.9 X |
| 3,225,082 | 12/1965 | McClure | 260/465.8 D X |
| 3,361,785 | 1/1968 | McClure | 260/465.8 D X |
| 3,484,475 | 12/1969 | Cornforth et al. | 260/465.8 D |
| 3,499,024 | 3/1970 | Morita et al. | 260/465.8 D X |
| 3,567,760 | 3/1971 | Feldman et al. | 260/465.8 D |
| 3,574,702 | 4/1971 | Feldman et al. | 260/465.8 D |
| 3,595,901 | 7/1971 | Smith | 260/465.9 |
| 3,671,569 | 6/1972 | Chabardes et al. | 260/465.8 D |

*Primary Examiner*—Joseph P. Brust

[57]  ABSTRACT

An unsaturated nitrile is reacted with an olefinic hydrocarbon in the presence of at least one organo derivative of a Group VA element as the sole reaction promoting material to yield unsaturated nitrile products having a greater number of carbon atoms than the unsaturated nitrile reactant.

10 Claims, No Drawings

METHOD OF PROMOTING THE REACTION OF UNSATURATED NITRILES WITH OLEFINS TO PRODUCE UNSATURATED NITRILES OF INCREASED CARBON NUMBER

This is a continuation-in-part of application Ser. No. 210,228, filed Dec. 20, 1971, now abandoned.

This invention relates to the reaction of an unsaturated nitrile and an olefinic hydrocarbon promoted by an organo derivative of a Group VA element.

Various methods of preparing high carbon number unsaturated nitrile reaction products are well known in the art. Representative methods include the reaction of unsaturated organic halides with metal cyanides, the reaction of unsaturated carbocyclic compounds with acrylonitrile in the presence of an alkaline catalyst, as well as the reaction of low carbon number unsaturated nitriles with olefins. In general, the methods of the art to date have not been completely satisfactory for various reasons. In some cases starting materials have been difficult to obtain, in other cases only certain nitriles are obtained because of the arrangement of carbon atoms in the carbocyclic nuclei, and in other cases the yields of the desired high carbon number unsaturated nitrile reaction products are often too low to be commercially attractive or advantageous.

It is an object of this invention to provide an improved process for the reaction of an olefinic hydrocarbon with an unsaturated nitrile in order to obtain an unsaturated reaction product having a greater number of carbon atoms than the original nitrile. Another object is to provide an improved process employing specific operating conditions which results in increased yields of high carbon number unsaturated nitrile reaction products. These and other objects of the invention will be readily apparent from the description and the appended claims.

In accordance with this invention, it has been found that improved yields of desired unsaturated nitrile reaction products are obtained by the reaction of at least one unsaturated nitrile and at least one olefinic hydrocarbon wherein the reaction is promoted by the presence of at least one organo derivative of a Group VA element, as the sole reaction promoting material.

One advantageous embodiment of this invention is that increased yields of 5-alkenenitriles are obtained by the reaction of 2-alkenenitriles with allylic olefins wherein the reactions are promoted by the presence of at least one organo derivative of the Group VA elements. Concurrently, minor amounts of corresponding isomeric, branched 4-alkenenitriles are produced.

The organo derivatives of the Group VA elements that can be employed as the sole reaction promoter in the practice of this invention are defined by the following formula $R''_n ZH_{3-n}$ wherein each R'' is independently selected from the group consisting of aryl, alkaryl, cycloalkylaryl, araryl, aryloxy, alkaryloxy, arylaryloxy; wherein each R'' group contains from 6 to 12 carbon atoms; Z is selected from the group consisting of

As, Sb, or Bi; and $n$ is 2 or 3. Illustrative of organo derivatives of the Group VA elements defined by the above formula are the following compounds: triphenylphosphine, diphenylphosphine, tris(hexylphenyl)phosphine, tris(cyclohexylphenyl)phosphine, dinaphthylphosphine, tris(4-biphenyl)phosphine, tris(4-butylphenyl)phosphine, triphenylamine, diphenylamine, tris(3,5-dipropylphenyl)amine, triphenylarsine, tris(pentylphenyl)arsine, triphenylbismuthine, diphenylarsine, 4-diphenylphosphinobiphenyl, tris(p-tolyl)stibine, tris(3,5-dimethylphenyl)bismuthine, diphenyl(4-ethylphenyl)phosphine, diphenoxy(phenyl)phosphine, diphenyl(p-methylphenoxy)phosphine, triphenylphosphite, diphenyl(p-tolyl)phosphine, triphenylphosphate, and the like, and mixtures thereof. The variant designated by $n$ in mixtures of promoters represented by the formula $R''_n ZH_{3-n}$ can vary, with the arithmetical sum of the value of $n$ of individual promoters, from 2 to 3. The term "reaction promoting material" includes materials commonly called catalysts as well as materials commonly called promoters.

The amount of promoter than can be employed in accordance with this invention can vary widely. In general, the mole ratio of promoter to unsaturated nitrile can vary from about 1 to 20 to about 1 to 1. Preferably, mole ratios of promoter to unsaturated nitrile reactant of from about 1 to 10 to about 1 to 3 are employed.

Any suitable mole ratio of olefinic hydrocarbon to unsaturated nitrile reactant can be employed in the practice of this invention. For example, acceptable olefinic hydrocarbon to nitrile ratios vary from about 2 to 1 to about 10 to 1, preferably from about 4 to 1 to about 6 to 1.

The reaction time can vary widely, e.g., from a few seconds to several hours, and preferably is within a range of from about 30 minutes to about 6 hours.

If desired, the process of this invention can be carried out in the presence of a solvent, diluent, or any generally inert environment. Typical solvents include aromatic hydrocarbons, such as benzene, toluene, p-xylene, o-xylene, m-xylene, ethylbenzene; aliphatic ethers, such as diethyl ether, ethyl propyl ether, dibutyl ether; cyclic ethers such as tetrahydrofuran and dioxane; or any other nonreactive solvent, such as cyclohexane, carbon tetrachloride, methylene chloride; and admixtures thereof. Although the use of a solvent or diluent is desirable, it is not necessary to the practice of this invention.

Any suitable reaction temperature can be employed in the practice of this invention. Reaction temperatures within the range of from about 100°C to 400°C are generally acceptable. Preferred reaction temperatures fall within the range of about 200°C to about 300°C.

Any suitable reaction pressure can be employed and can vary over a wide range. In general, the reaction pressures will be within the range of from about atmospheric to about 100,000 psig, preferably from about 1,000 to about 4,000 psig.

If desired, the processes of this invention can be carried out in the presence of a polymerization inhibitor. The use of the inhibitor often advantageously limits side reactions such as the dimerization or polymerization of the unsaturated nitrile. When an inhibitor is employed, it is generally desirable that an amount of from about 0.001 to about 5, preferably from about 0.1 to about 1, percent by weight inhibitor based on the weight of unsaturated nitrile reactant be employed. Suitable inhibitors include hydroquinone, 2,6-di-tert-butyl-para-cresol, 2,6-di-tert-butylhydroquinone, 4- tert-butyl-catechol, para-hydroxydiphenylamine, and the like, and combinations thereof.

Any olefinic hydrocarbon compound can be employed in the practice of this invention, provided that the compound has at least one olefinic linkage having joined to one of the doubly bonded carbons a carbon atom containing at least one hydrogen atom attached thereto. The olefinic hydrocarbons preferably have from 3 to 12 carbon atoms per molecule with from 1 to 2 ethylenically unsaturated nonconjugated double bonds as the sole aliphatic unsaturation. The preferred types of these compounds are the open chain monoolefinic hydrocarbons represented by the formula $R_2C=CR-CHR_2$, wherein each R is independently selected from the group consisting of hydrogen, alkyl, cycloalkyl, and aryl hydrocarbyl radicals and combinations thereof. Especially preferred are those monoolefinic hydrocarbons having 3 to 12 carbon atoms and having an alkyl group, preferably methyl, as a side chain attached to at least one of the carbon atoms comprising the ethylenic linkage. Specific examples of unsaturated compounds of this type which are used in the process of this invention include propylene, isobutylene, diisobutylene, triisobutylene, beta-pinene, tetramethylethylene, 2-butene, biallyl, bimethallyl, alpha-methylstyrene, 1-pentene, 1-decene, cyclohexene and allylbenzene.

Any unsaturated nitrile can be employed in the practice of this invention provided the nitrile contains ethylenic unsaturation, contains at least one hydrogen atom attached to a doubly bonded carbon atom, and contains at least one cyano group attached to a carbon atom adjacent and doubly bonded to a carbon atom containing at least one hydrogen atom. Illustrative unsaturated nitrile reactants are those represented by the formula

wherein each R' is independently selected from the group consisting of hydrogen, alkyl, cycloalkyl, and aryl hydrocarbyl radicals or combinations thereof, such as alkylcycloalkyl, cycloalkylalkyl, aralkyl and arylcycloalkyl radicals. Preferably the total number of carbon atoms in the nitrile reactant is within the range of from 3 to 18, more preferably from 3 to 8. Examples of unsaturated nitriles meeting the requirements of the above formula are acrylonitrile, 2-butenenitrile, 2-hexenenitrile, 5-methyl-2-hexenenitrile, 4-methyl-2-heptenenitrile, 6,6,8,8-tetramethyl-2-nonenenitrile, 6-cyclohexyl-2-octenenitrile, 6-phenyl-2-decenenitrile, 2-octadecenenitrile, 6,7,8-trimethyl-9-phenyl-2-nonenenitrile, and the like, and mixtures thereof.

In the process of the present invention it is believed that the olefinic hydrocarbon compound and the unsaturated nitrile react in accordance with the ene reaction to produce, as the principal product, a compound having the structural formula

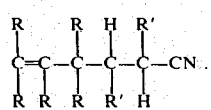

Generally, a lesser amount of an isomeric product having the formula

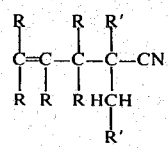

is also produced. Thus, isobutylene and acrylonitrile react to produce 5-methyl-5-hexenenitrile as the principal product along with a small amount of 2,4-dimethyl-4-pentenenitrile. It can be readily seen that isobutylene as the olefinic hydrocarbon reactant possesses six of the required allylic hydrogens but that all six are structurally equivalent so that only two compounds corresponding to the above general formulas are produced according to the ene reaction. However, it will also be evident that if a compound having two or more allylic hydrogens which are not structurally equivalent is employed as the olefinic hydrocarbon reactant, the number of expected isomeric product compounds having the above general formulas will be increased. For example, if 2,4,4-trimethyl-1-pentene is reacted with acrylonitrile the major products expected according to the ene reaction would be 5-methylene-7,7-dimethyloctanenitrile and 4-methylene-2,6,6-trimethylheptanenitrile with lesser amounts of 5,7,7-trimethyl-5-octenenitrile and 2,4,6,6-tetramethyl-4-heptenenitrile. Other factors not fully understood at present may influence the relative amounts of the possible isomers in the product and in other instances presently employed analytical methods may not distinguish the various isomers present. Indeed, the products find utility in many applications with no need of a costly separation of the isomers present in the product.

A convenient method of carrying out this invention comprises heating a mixture of a 2-alkenenitrile, e.g., acrylonitrile, and an olefinic hydrocarbon compound, e.g., isobutylene, present in a mole ratio of about 1 to 5, respectively, in a reaction pressure vessel at a temperature within the range of 200° to 300°C and at pressures of from 1,000 to 4,000 psig. Thereafter, the resulting unsaturated nitrile reaction product is readily isolated from the reaction mixture by any convenient product recovery method, such as fractional distillation. The reaction of olefinic hydrocarbons and unsaturated nitriles can be promoted indefinitely, in apparatus well known to the art and suited to either batch or continuous reaction conditions, until one or both of the reactants, i.e., the nitrile and/or the olefinic hydrocarbon constituent, are depleted from the reaction media.

This invention is illustrated further by the following examples.

COMPARATIVE EXAMPLE A

A mixture of acrylonitrile (5.3 g., 0.1 mole, containing 0.5 weight percent hydroquinone), 2,4,4-trimethyl-1-pentene (33.6 g., 0.3 mole) and n-octane (5.0 g.) was placed in a 300 ml autoclave. The autoclave was closed, purged of air with nitrogen, pressured to 400 psig with nitrogen and heated at 240°C for 4 hours. Analysis by gas-liquid chromatography indicated at 60.3 percent conversion of acrylonitrile and a 3.10 g. (18.8 percent of theory, 31.2 percent ultimate) yield of 5-methylene-7,7-dimethyloctanenitrile. Also indicated was a 1.6 percent ultimate yield of the isomer 4-methylene-2,6,6-trimethylheptanenitrile and a 0.5 percent yield of two other isomers.

EXAMPLE I

A mixture of acrylonitrile (5.3 g., 0.1 mole, containing 0.5 weight percent hydroquinone), 2,4,4-trimethyl-1-pentene (33.6 g., 0.3 mole), triphenylphosphine (5 g., 0.019 mole) and n-octane (5.0 g.) was added to a 300 ml autoclave. The autoclave was closed, the air displaced by nitrogen, the mixture was pressured to 400 psig with nitrogen and heated at 240°C for 4 hours. Analysis by gas-liquid chromatography indicated an 82.3 percent conversion of acrylonitrile and a 6.57 g. (39.8 percent of theory, 48.3 percent ulitmate) yield of 5-methylene-7,7-dimethyloctanenitrile. Also indicated was a 2.6 percent ultimate yield of the isomer 4-methylene-2,6,6-trimethylheptanenitrile and about 0.8 percent yield of two other isomers.

As shown by comparison of Example I with Comparative Example A, the yield of 5-methylene-7,7-dimethyloctanenitrile is significantly increased when triphenylphosphine is employed to promote the reaction of the olefinic hydrocarbon and the unsaturated nitrile.

EXAMPLE II

Acrylonitrile (40 g., 0.75 mole, containing 0.1 percent hydroquinone), diphenylamine (80 g., 0.473 mole) and benzene (200 g.) were charged to a 1-liter stainless steel autoclave. The autoclave was closed, purged of air with nitrogen, and isobutylene (210 g., 3.75 moles) was added. This mixture was stirred and maintained at 270°C for 3 hours during which the maximum pressure reached was 2400 psig. Analysis by gas-liquid chromatography of the product mixture indicated a 95 percent conversion of acrylonitrile, and yields of 5-methyl-5-hexenenitrile (55.3 g., 67.3 percent of theory) and 2,4-dimethyl-4-pentenenitrile (3.89 percent of theory) were obtained.

As illustrated by this example, diphenylamine is an effective promoter of the reaction of olefinic hydrocarbons with unsaturated nitriles.

EXAMPLES III TO IX

Isobutylene and acrylonitrile were combined and reacted in the presence of benzene and various promoters in accordance with the procedure described in Example II. Tabulated in the table hereinafter are the results.

The foregoing Examples III through IX illustrate the uniformly high yields of unsaturated nitrile reaction product obtained under reaction conditions which vary the amount of nitrile and/or olefinic hydrocarbon reactant and the type of organo Group VA element promoter.

COMPARATIVE EXAMPLE B

A one-liter autoclave was charged with 5 g. triphenylphosphine, 80 g. acrylonitrile, and 100 ml benzene. The system was flushed with nitrogen, charged with 30 g. ethylene and heated at 260°C for two hours. The reactor was cooled, vented and the liquid phase distilled at atmospheric pressure. The overhead material was collected and was found to be a mixture of about 72 g. benzene and 78 g. acrylonitrile. The distillation which weighed 7 g. was analyzed by gas-liquid chromatography (GLC) to reveal that it consisted essentially of triphenylphosphine and a small amount of the acrylonitrile dimer

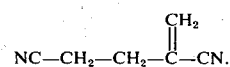

Thus, no product was found which could be attributed to the reaction of ethylene with acrylonitrile.

COMPARATIVE EXAMPLE C

A one-liter autoclave was charged with 100 ml benzene and 20 g. triphenylphosphine. The system was flushed with nitrogen, charged with 200 g. isobutylene and heated at 250°C for 2 hours. No pressure drop was observed during the reaction period. The autoclave was cooled, vented and the liquid phase distilled at atmospheric pressure. The overhead product, all collected at 75°–80°C, weighed 75 g. and the distillation residue which solidified weighed 20.2 g. GLC analysis showed the overhead material to be benzene and the residue to be triphenylphosphine. No other products were observed thus showing that isobutylene alone was unreactive under conditions suitable for the reaction of isobutylene with acrylonitrile according to this invention.

COMPARATIVE EXAMPLE D

A one-liter autoclave was charged with 100 g. benzene, 10 g. triphenylphosphine, 53 g. acrylonitrile, 208

TABLE I

| Example | Reaction of Acrylonitrile with Isobutylene | | | | | | |
|---|---|---|---|---|---|---|---|
| | III | IV | V | VI | VII | VIII | IX |
| Isobutylene, moles | 3.85 | 3.83 | 4.0 | 3.95 | 3.75 | 3.95 | 3.75 |
| Acrylonitrile, moles | 0.75 | 0.75 | 0.75 | 0.75 | 0.75 | 1.51 | 0.75 |
| Benzene, g. | 200[1] | 200 | 200 | 200 | 200 | 180 | 200 |
| Promoter | $Ph_3P$[2] | $Ph_3P$ | $Ph_2NH$[3] | $Ph_2NH$ | $Ph_3P$ | $Ph_3P$ | $Ph_2NH$ |
| Promoter, moles | 0.152 | 0.152 | 0.118 | 0.118 | 0.076 | 0.114 | 0.472 |
| Temperature, °C | 270 | 270 | 270 | 270 | 270 | 260 | 270 |
| Initial (maximum) pressure, psig | 2500 | 2500 | 2900 | 2500 | 2380 | 2400 | 2400 |
| Time, hours | 3 | 3 | 3 | 3 | 3 | 5 | 3 |
| Conversion of acrylonitrile, Wt. % | 92 | 88 | 97 | 96 | 87 | 95 | 95 |
| Yield, 5-methyl-5-hexenenitrile | | | | | | | |
| Per pass | 65.9 | 64.8 | 64.1 | 60.8 | 60.1 | 60.1 | 67.3 |
| Ultimate | 71.7 | 73.6 | 66.2 | 63.2 | 69.0 | 63.1 | 70.8 |
| Ultimate yield, 2,4-dimethyl-4-pentenenitrile | 4.8 | 5.0 | 4.0 | 4.9 | 4.3 | —[4] | 4.7 |

[1] toluene rather than benzene
[2] triphenylphosphine
[3] diphenylamine
[4] not determined g. styrene, and 0.1 g. hydroquinone. The system was flushed with nitrogen, pressured to 500 psig with nitrogen and heated at 250°C for 2 hours. The autoclave was cooled, vented and opened. The reaction mixture had become an intractable tar which was discarded. This result shows that styrene is unsuitable as an olefinic hydrocarbon reactant for preparing the higher molecular weight nitriles according to the process of this invention.

The higher carbon number nitriles produced according to this invention have utility as intermediates for the production of monoamines and monocarboxylic acids by methods well known in the art. Such monoamines and monocarboxylic acids have numerous known uses in the chemical arts. In addition the higher carbon number nitrile products can be converted to unsaturated dinitriles which in turn can be converted to saturated diamines or dicarboxylic acids according to well known procedures. Such diamines and dicarboxylic acids have utility in forming polyamides suitable for use as fibers, and preparing molded articles.

Reasonable variations and modifications are possible within the scope of the foregoing disclosure and the appended claims to the invention.

We claim:

1. A method which comprises reacting under suitable reaction conditions at least one olefinic hydrocarbon compound with at least one unsaturated nitrile reactant in the presence of, as the sole reaction promoting material, a promoter consisting essentially of at least one organo derivative of a Group VA element, said reaction conditions being suitable for the reaction of said at least one olefinic hydrocarbon compound with said at least one unsaturated nitrile reactant to produce at least one unsaturated nitrile product having a greater number of carbon atoms than said unsaturated nitrile reactant;

said at least one olefinic hydrocarbon compound having from 3 to 12 carbon atoms and being represented by the formula $R_2C=CR-CHR_2$, wherein each R is independently selected from the group consisting of hydrogen, alkyl, cycloalkyl, and aryl hydrocarbyl radicals and combinations thereof;

said at least one unsaturated nitrile reactant having from 3 to 18 carbon atoms and being represented by the formula $R'CH=CR'-CN$ wherein each R' is selected from the group consisting of hydrogen, alkyl, cycloalkyl, and aryl hydrocarbyl radicals and combinations thereof;

said organo derivative of a Group VA element being represented by the formula $R''_nZH_{3-n}$ wherein each R'' is independently selected from the group consisting of aryl, alkaryl, cycloalkylaryl, araryl, aryloxy, alkaryloxy, and arylaryloxy; each R'' group containing from 6 to 12 carbon atoms; Z is selected from the group consisting of $$N, P, \overset{O}{\overset{\|}{P}}, As, Sb, and Bi;$$

and $n$ is selected from the integers 2 and 3.

2. A method in accordance with claim 1 wherein said reaction conditions comprise a temperature in the range of about 200°C to about 300°C, a pressure in the range of about 1000 to about 4000 psig, a contact time in the range of about 30 minutes to about 6 hours, a mole ratio of said olefinic hydrocarbon compound to said unsaturated nitrile reactant in the range of about 4:1 to about 6:1, and a mole ratio of said promoter to said unsaturated nitrile reactant in the range of about 1:10 to about 1:3.

3. A method which comprises reacting under suitable reaction conditions an olefinic hydrocarbon compound with an unsaturated nitrile reactant in the presence of, as the sole reaction promoting material, a promoter consisting essentially of at least one organo derivative of a Group VA element to produce, as the principal product of the reaction, at least one unsaturated nitrile product having a greater number of carbon atoms than said unsaturated nitrile reactant;

said olefinic hydrocarbon compound having from 3 to 12 carbon atoms and being represented by the formula $R_2C=CR-CHR_2$, wherein each R is independently selected from the group consisting of hydrogen, alkyl, cycloalkyl, and aryl hydrocarbyl radicals and combinations thereof;

said unsaturated nitrile reactant having from 3 to 18 carbon atoms and being represented by the formula $R'CH=CR'-CN$ wherein each R' is selected from the group consisting of hydrogen, alkyl, cycloalkyl, and aryl hydrocarbyl radicals and combinations thereof;

said organo derivative of a Group VA element being represented by the formula $R''_nZH_{3-n}$ wherein each R'' is independently selected from the group consisting of aryl, alkaryl, cycloalkylaryl, araryl, aryloxy, alkaryloxy, and arylaryloxy; each R'' group containing from 6 to 12 carbon atoms; Z is selected from the group consisting of $$N, P, \overset{O}{\overset{\|}{P}}, As, Sb, and Bi;$$

and $n$ is selected from the integers 2 and 3;

said reaction conditions comprising a temperature in the range of about 100°C to about 400°C, a pressure in the range of about atmospheric to about 100,000 psig, a contact time in the range of about 30 minutes to about 6 hours, a mole ratio of said olefinic hydrocarbon compound to said unsaturated nitrile reactant in the range of about 2:1 to about 10:1, and a mole ratio of said promoter to said unsaturated nitrile reactant in the range of about 1:20 to about 1:1; and said principal product consisting of at least one compound having the structural formula

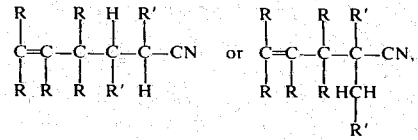

wherein R and R' are as defined above.

4. A method in accordance with claim 3 wherein said reaction conditions further comprise a solvent or diluent.

5. A method in accordance with claim 3 wherein said olefinic hydrocarbon compound is isobutylene, said unsaturated nitrile reactant is acrylonitrile, said promoter is triphenylphosphine, and said principal product is 5-methyl-5-hexenenitrile.

6. A method in accordance with claim 3 wherein said olefinic hydrocarbon compound is 2,4,4-trimethyl-1-pentene, said unsaturated nitrile reactant is acrylonitrile, said promoter is triphenylphosphine, and said principal product is 5-methylene-7,7-dimethyloctanenitrile.

7. A method in accordance with claim 3 wherein said olefinic hydrocarbon compound is isobutylene, said unsaturated nitrile reactant is acrylonitrile, said promoter is diphenylamine, and said principal product is 5-methyl-5-hexenenitrile and 2,4-dimethyl-4-pentenenitrile.

8. A method in accordance with claim 3 wherein said promoter is triphenylphosphine.

9. A method in accordance with claim 3 wherein said promoter is diphenylamine.

10. A method in accordance with claim 3 wherein Z is P.

* * * * *

UNITED STATES PATENT AND TRADEMARK OFFICE
CERTIFICATE OF CORRECTION

PATENT NO. : 3,996,262
DATED : December 7, 1976
INVENTOR(S) : Stanley D. Turk; Charles A. Drake It is certified that error appears in the above-identified patent and that said Letters Patent are hereby corrected as shown below:

Column 8, line 22, delete R'CH=R'-CN and insert -- R'CH=CR'-CN --

Signed and Sealed this

Eleventh Day of September 1979

[SEAL]

Attest:

LUTRELLE F. PARKER
Attesting Officer   Acting Commissioner of Patents and Trademarks